United States Patent
Huys et al.

(10) Patent No.: US 8,962,304 B2
(45) Date of Patent: Feb. 24, 2015

(54) INTERFACE DEVICE AND METHOD FOR USING THE SAME

(75) Inventors: Roeland Huys, Wilsele (BE); Wolfgang Eberle, Leuven (BE); Carmen Bartic, Wilsele (BE)

(73) Assignee: IMEC, Leuven (BE)

( * ) Notice: Subject to any disclaimer, the term of this patent is extended or adjusted under 35 U.S.C. 154(b) by 1269 days.

(21) Appl. No.: 12/039,593

(22) Filed: Feb. 28, 2008

(65) Prior Publication Data

US 2009/0004685 A1    Jan. 1, 2009

Related U.S. Application Data

(60) Provisional application No. 60/892,071, filed on Feb. 28, 2007.

(30) Foreign Application Priority Data

Sep. 14, 2007    (EP) .................................... 07116467

(51) Int. Cl.
    C12M 1/34       (2006.01)
    C12M 3/00       (2006.01)
    G01N 33/483     (2006.01)
    G01N 33/543     (2006.01)
    G01N 33/50      (2006.01)

(52) U.S. Cl.
    CPC ........ *G01N 33/4836* (2013.01); *G01N 33/5436* (2013.01); *G01N 33/5008* (2013.01)
    USPC .......................................... 435/287.1; 435/29

(58) Field of Classification Search
    CPC ................. G01N 33/54366; G01N 33/54373; G01N 33/5008; G01N 33/5011; B01J 2219/00722; B01J 19/0046; B82Y 30/00; C12Q 1/04; C12Q 1/18
    USPC ................................................ 435/29, 287.1
    See application file for complete search history.

(56) References Cited

U.S. PATENT DOCUMENTS

| | | | |
|---|---|---|---|
| 2002/0127733 A1 | 9/2002 | Kovacs | |
| 2005/0029099 A1 | 2/2005 | Eversmann et al. | |
| 2006/0105373 A1* | 5/2006 | Pourmand et al. | 435/6 |
| 2007/0095671 A1 | 5/2007 | Kovacs | |

FOREIGN PATENT DOCUMENTS

| | | |
|---|---|---|
| EP | 1 723 983 A1 | 11/2006 |
| WO | 0133201 A1 | 5/2001 |

OTHER PUBLICATIONS

Extended European Search Report in EP 08152100.7 mailed May 21, 2008.
European Search Report for EP 07 11 6457 completed Feb. 4, 2008.
(Continued)

*Primary Examiner* — Michael Hobbs
(74) *Attorney, Agent, or Firm* — McDonnell Boehnen Hulbert & Berghoff LLP

(57) ABSTRACT

The present disclosure is related to an interface device for providing access to a network to be monitored. The interface device includes a plurality of elements, the elements being sensors and/or actuators. A selection circuit is provided for selecting a subset of elements among the plurality of elements, each element of the subset being arranged for outputting and/or receiving a signal. A local memory is provided for storing the subset.

14 Claims, 5 Drawing Sheets

(56) References Cited

OTHER PUBLICATIONS

Lambacher, A., et al., "Electrical Imaging of Neuronal Activity by Multi-Transistor-Array (MTA) Recording at 7.8 μm Resolution," Appl. Phys. A. 79, 1607-1611 (2004).

Berdondini, L., et al., "High-Density Electrode Array for Imaging in Vitro Electrophysiological Activity," Biosensors and Bioelectronics, vol. 21, Issue 1, Jul. 15, 2005, pp. 167-174.

Eversmann B. et al., "A 128×128 CMOS Biosensor Array for Extracellular Recording of Neural Activity," IEEE J. Solid-State Circuits, vol. 38, No. 12, pp. 2306-2317 (Dec. 2003).

* cited by examiner

INTERFACE DEVICE AND METHOD FOR USING THE SAME

The present application claims the priority of U.S. Provisional Patent Application No. 60/892,071 filed Feb. 28, 2007, and of European Patent Application No. EP 07116467.7, filed Sep. 14, 2007.

BACKGROUND

The present disclosure relates to the field of interface devices comprising a plurality of sensors and/or actuators.

In many cell-physiological and medical applications, there is a desire to measure biochemical parameters in the close vicinity of living cells.

A popular neurons-on-chip technique is the Multi-Electrode Array (MEA). MEAs are made of an insulating substrate (e.g. glass), with a maximum of around 100 electrodes and a minimal electrode pitch of around 10 μm. MEAs do not contain active sensors, so all electrodes have to be connected to an external amplifier.

In order to perform experiments on large networks of hippocampal neurons, pitch sizes (representing the distance between two neurons) of less than 10 μm and array sizes of more than 10K sensors have to be used. Such experiments call for the use of active sensor arrays.

More recent designs are made of a few planar sensors based on ISFET-transistors. An ISFET-transistor is a MOSFET-transistor wherein the gate electrode is replaced by an electrolyte solution, enabling the transistor to sense charges present at the oxide surface.

An active large sensor array is developed in 'A 128×128 CMOS Biosensor Array for Extracellular Recording of Neural Activity' (Eversmann B. et al., *IEEE J. Solid-State circuits*, pp. 2306-2317, December 2003). A 128×128 matrix of sensors based upon OSFET (Oxide-Semiconductor Field Effect) transistors is presented. The sensors have a pitch of 7.8 μm and the chip can support a total multiplexed sampling rate of 32 MS/s, enabling the read-out of the whole array in 500 μs which is equal to a frame rate of 2K frames per second.

A large analogue readout circuit can raise matching problems: two sensor circuits located a certain distance apart can show different amplification factors and bias offsets. The sensors produce signals with very low amplitudes, which impose noise problems. Further, the sensors measure a signal with respect to a common reference electrode, whereby the signal comprises the signal of interest, noisy signals from neighbouring cells, and interference from the environment.

SUMMARY

The present disclosure aims to present an interface device for providing access to a network being monitored, such as a network of neurons, whereby the interface device is arranged for culturing, stimulating, and detecting living cells. One possible application of such a device is in the field of neurophysiology, as it could allow one to run experiments on thousands of neurons simultaneously.

In one embodiment, the interface device comprises a plurality of elements. These elements can be sensors and/or actuators. The interface device further comprises a selection means and a local memory. The selection means selects a subset of elements among the plurality of elements. The local memory stores the selected subset. Each element of the subset is arranged for outputting and/or receiving a signal. By using a local memory storing a pattern of elements of interest, an efficient architecture read-out is provided instead of scanning the entire architecture. Classically, a local multiplexing strategy could be used with a single row/column operation: selecting one sensor, performing readout and selecting the next sensor, in a time-multiplexing method. However, this would call for a row/column write operation for each sample and each sensor and/or actuator. Using high A/D sampling rates (e.g. 10 Ksps) would result in mixed-signal switch noise problems.

In an embodiment, the plurality of elements and the local memory are implemented as a block and the interface device comprises a plurality of said blocks. The region of interest can be expanded. Due to the nature of the experiments, only a small portion of the total number of sensors is actually useful. It is sufficient to select only the sensors and/or actuators of interest and leave the others unconnected.

In an embodiment, the block further comprises at least one differential amplifier. The differential amplifiers are fed by output signals of the selected elements, providing local differential signals. By using local differential amplifiers, a local electric potential across two sensors is measured rather than the potential between one sensor and a reference (e.g. ground, supply). This way, interference can be cancelled because the interference is present on the common-mode. The differential amplifiers are preferably fed with output signals of elements in the close vicinity. Because the differential signal is measured locally, matching problems between two sensors are limited. Therefore the amplifiers can be biased in the optimal operating region and bias offsets at the input nodes are cancelled. High amounts of data traffic and row/column switching in the architecture produces switch noise in the analogue circuits.

In an alternative embodiment, the interface device comprises a reference element. The reference element belongs to the plurality of elements and is arranged for generating a reference signal for the differential amplifier. Further, in each block an element can be selected as a reference element providing a reference signal. In a block the reference signal is fed to each of the differential amplifier of that block. The noise level is reduced when using local differential amplifiers whereof one side is connected to the same reference sensor (providing the same reference signal/voltage).

In an embodiment a block may further comprise a biasing circuit. Each bias circuit is implemented to provide a proper bias to the differential amplifier. The output of each amplifier may be buffered to provide enough drive current to put the analogue signal on the chip-wide output bus. Only the selected elements put their signals on the output buses. By selecting accurately these elements and by working locally (local memory, local bias circuit and local amplification), the interface device is arranged for monitoring (e.g. reading out, actuating, etc.) a high density sensor and/or actuator array very quickly.

The interface device may further comprise output multiplexers receiving signals from the buses. A set of analogue buses is selected to send the output of the chip for decoding.

The interface device is arranged for giving access to a network of neurons. The interface device is designed to reduce present noise and interference. The interface device can be used in all applications in which a high density matrix is desired in combination with a low density readout, such as multiple sensing devices, camera applications, driving electronics, artificial analogue neural networks. Typically the interface device can for example be applied in multiple sensing devices, particle detection, bio-sensor arrays (e.g. DNA arrays), neurons on chip, and artificial analogue neural networks.

The present disclosure further provides a method for accessing a signal in the interface device. The method comprises the steps of: a) determining a selection of elements forming a subset, where each element of the subset is arranged for generating and/or receiving a signal, b) storing the subset in a local memory and c) accessing at least one element of the stored subset for accessing the signal. Typically, several elements are accessed consecutively. Cells behave quasi-statically: once the subset of interesting sensors is determined, this subset or pattern remains constant for a long time. Small updates can be required for slow movements of the cells. The method shows the advantage of a local memory: by performing a set of row/column selection operations, it is possible to select a subset or local pattern of elements stored in a local memory (or in one memory bit for each element).

In an embodiment the method further comprises the step of selecting a reference element in the subset. This reference element is arranged for generating and/or receiving a reference signal. Further, the method comprises the step of feeding a differential amplifier with the signal and the reference signal.

These method steps can be used to access a network of electrically-active cells, such as neurons, cardiomyocytes, or tumor cell lines.

DETAILED DESCRIPTION

In many cell-physiological and medical applications, there is a desire to measure, detect, and/or stimulate biochemical parameters in the close vicinity of living cells. These parameters can be measured with different kinds of biosensors. The present disclosure provides sensors that, in preferred embodiments, display the following properties:

The sensors are preferably scaled to a size that approaches the dimensions of one cell or a region-of-interest of this cell.
The sensors are preferably located in close vicinity of the cells.
The sensors are preferably amenable to use where cells may be located in randomly scattered structures.
Preferably, it is possible to read out the data of many sensors simultaneously in an automated way.

The present disclosure proposes an interface device with specific improved design for the above mentioned types of applications. It further proposes a method for using a system having the above-mentioned properties. The interface device provides access to a network to be monitored.

Figure 1:
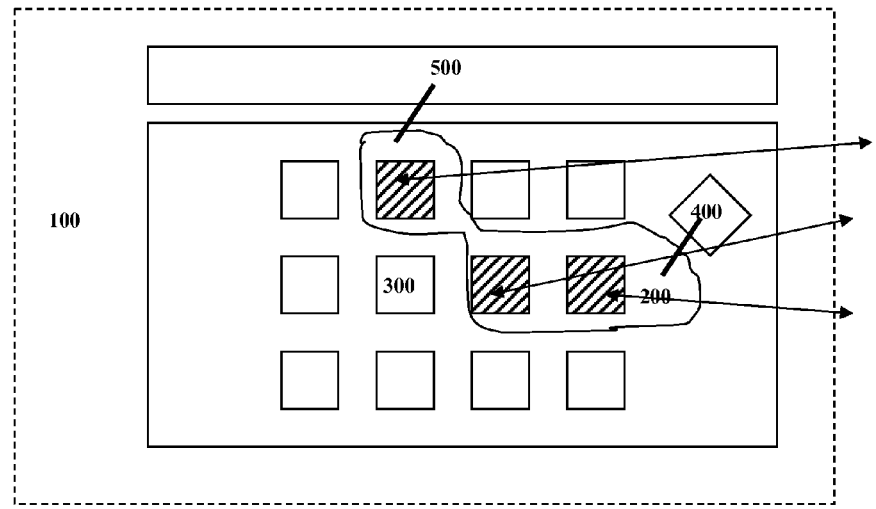
FIG. 1 is a schematic plan view of an embodiment of an interface device.
Figure 2:
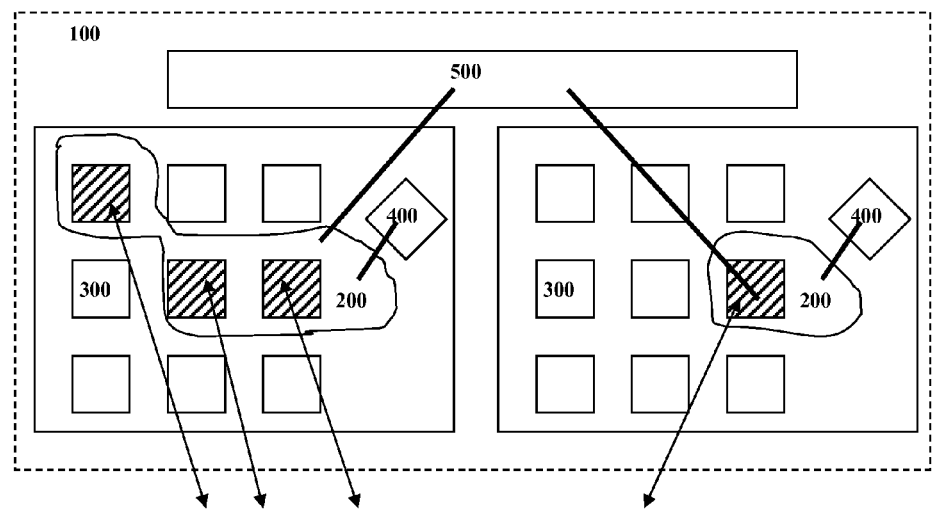
FIG. 2 is a schematic plan view of another embodiment of an interface device.

One embodiment of such an interface device is schematically shown in FIG. 1. The interface device 100 comprises a plurality of elements 300. These elements 300 can be sensors and/or actuators. The interface device further comprises a selection means 500 and a local memory 400. The selection means selects 500 a subset 200 of elements among the plurality of elements. The local memory 400 stores the subset. Each element of the subset is arranged for outputting and/or receiving a signal. By using a local memory storing a pattern of elements of interest, an efficient architecture read-out is provided instead of scanning the entire network. A denser or bigger network can be divided in blocks wherein each block comprises a number of elements and a local memory. This is presented in FIG. 2.

Different features of various embodiments include a) local multiplexing, b) localized memory and parallel readout and/or c) localized differential amplification. Each of these is discussed more in detail below.

A. Local Multiplexing

Due to the nature of many sorts of experiments, only a small portion of the total number of sensors may actually be useful. It is sufficient, then, to select only the sensors of interest and leave the others unconnected.

Figure 3:
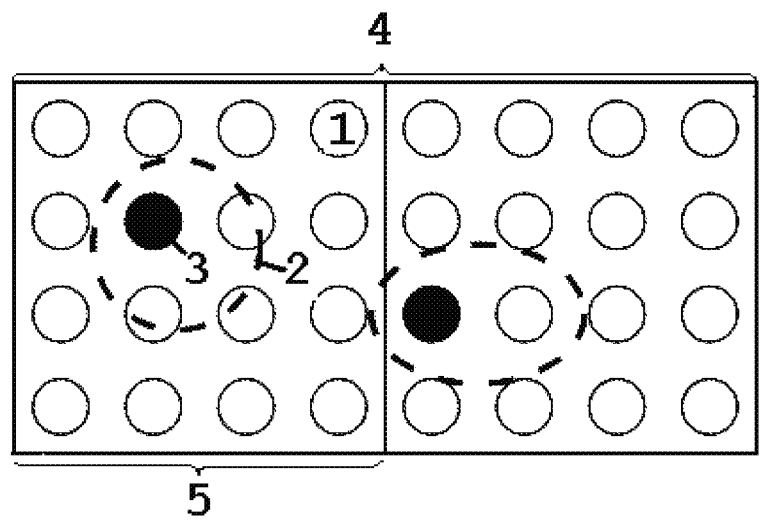
FIG. 3 is a schematic plan view of an array with different sensors.

From FIG. 3, it can be seen that by using a distance between sensors 1 (white circles) that is smaller than half the size of a biological cell 2 (dashed circle), it can be guaranteed that there will be a sensor underneath the cell. Despite the fact that there are many sensors in this array, it is only necessary to read out one sensor 3 (black circle) in a certain area (rectangle 4) because the cells have an average spacing that is larger than the sensor spacing. This is performed by dividing the matrix into smaller matrices, where only one sensor is selected for read-out, and the others are left unconnected. One such a small matrix is called 'microcell' 5 in this description.

The actual dimensions are dependent on the application. For example for experiments with hippocampal neurons for in-vitro cell culture conditions, following parameters can be used:

3 μm sensor diameter
6 μm sensor spacing (pitch)
24 μm microcell size (4×4 sensors for each microcell)

For each microcell 5, a local multiplexing circuit, a bias circuit, an amplifier and a proper logic circuit are be provided.

B. Localized Memory and Parallel Readout

In theory, a local multiplexing strategy could be used with a single row/column operation: selecting one sensor, performing readout and selecting the next sensor, in a time-multiplexing method. However, this would require a row/column write operation for each sample and each sensor. Using high A/D sampling rates (e.g. 10 Ksps) would result in mixed-signal switching noise problems.

Cells behave quasi-statically: once the pattern of interesting sensors is defined, this pattern remains relatively constant for a long time. Only small, incremental updates may be required in situations were movement of the cells is relatively slow. Furthermore, correlated signals due to cell phenomena behave slowly with respect to the A/D sampling rates. For most applications, it is not necessary to read out a big area at once. One or a few smaller regions of interest are sufficient. An example of such phenomena is the reading of action potentials in neurons. The time required for a signal to travel from one neuron to another can take 1 ms to 100 ms.

The topology of sensor devices described herein makes use of a local memory to store the pattern of active sensors in the microcells. By selecting the region of interest (e.g., a part of a neural network to be monitored), a set of sensors can be selected at the same instant of time, with the possibility of reading out a large number of sensors simultaneously. This is shown in FIG. 4.

Figure 4:
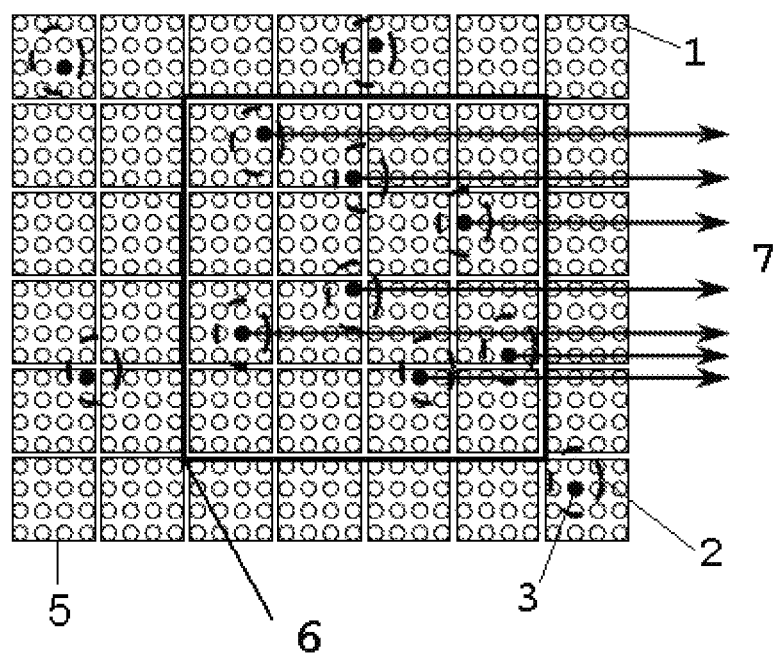
FIG. 4 represents schematically a selection of active sensors.

The small white circles in FIG. 4 represent unused sensors 1. The small black circles represent used (and thus connected) sensors. The bigger dashed circles represent cells 2. The small rectangles represent microcells 5, while the big rectangle represents a set of adjacent of microcells called a macrocell 6. The arrows 7 illustrate analogue signals being distributed to the exterior world.

This concept shows an advantage of local memory: by performing a set of row/column selection operations, it is possible to select a local pattern of sensors stored in one memory bit for each sensor. The pattern of sensors can be connected to an analogue amplifier and buffer and the signal can be transported outside the chip. This results in a large reduction of switching noise.

In an example, a macrocell is defined by an area of 4×4 microcells. Each microcell comprises 4×4 sensors. Only one sensor is active in each microcell, so at most 16 analogue signals need be read out simultaneously. This reduces the matrix row/column switch traffic by a factor of 16.

The macrocell can be selected by providing a row/column addressing matrix with one row/column crosspoint for each microcell. A macrocell can be selected by enabling a range of microcell row selection lines and a range of microcell column selection lines.

C. Local Differential Readout

Figure 5:
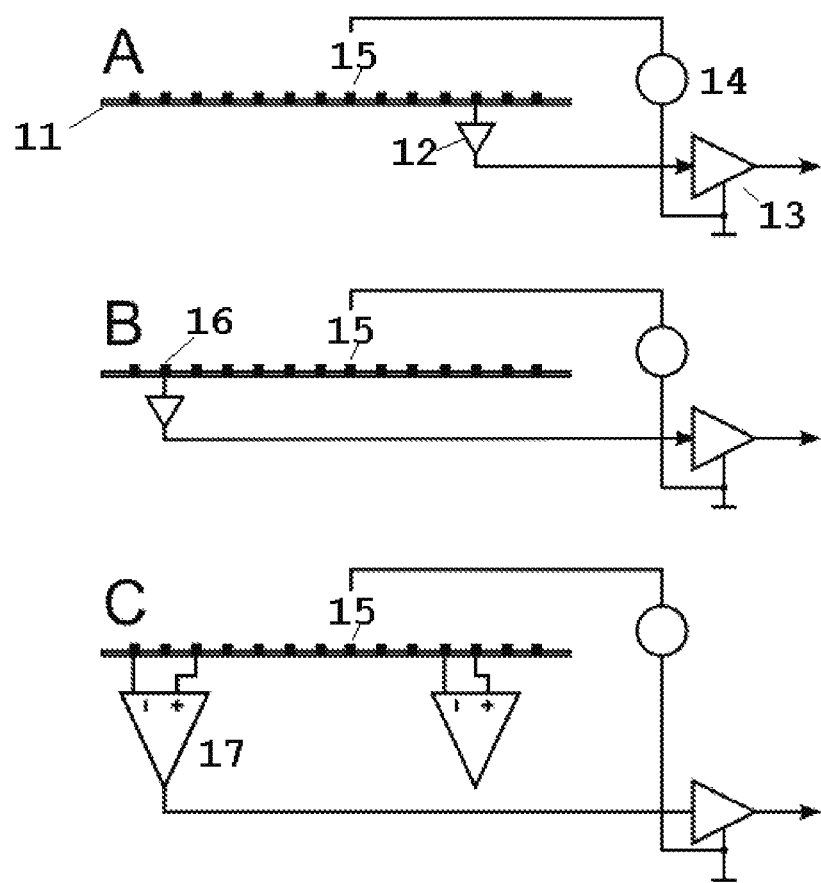
FIG. 5 is a schematic diagram illustrating the logic of a local differential read-out technique.

The principle of local differential readout is exemplified by FIG. 5. A sensor surface 11 is displayed (side view) with an array of sensors on top of it. A physiological medium with cells or tissues is located on top of the sensor surface. Circuits are located below the sensor surface.

To each sensor, a local amplification, bias and buffer circuit, all comprised in 12, is connected. This is done to provide enough output drive to transport the sensor signal on a long line outside the matrix. Further, another amplification and buffer circuit, 13, is connected to one sensor.

A DC source 14 is added to set the physiological medium on a proper operation voltage to bias the input circuits. The physiological medium is connected to the electrical circuits by a reference electrode 15.

In FIG. 5B, another sensor 16 at another location on the surface is selected, in a short time instant. FIG. 5C shows a local differential amplifier 17.

In FIG. 5A, the single-ended amplifier 13 measures the potential between the output of circuit 12 and ground. All interference captured by the loop created via 14 and 15 is amplified.

Switching of the amplifier input to another sensor occurs in FIG. 5B. The local amplifiers make use of a bias circuit. Due to the matching transistor offset and the sensor parameters across the sensor array surface, there can be large differences when comparing signal offset and amplitude between two sensor outputs. When switching from one sensor to another across the matrix, the output amplifier input stage operates in another region. This can result in distortion and clipping of the signal.

By using local differential amplifiers, a local electric potential across two sensors can be measured rather than the potential between one sensor and the ground, as illustrated in FIG. 5C. In this way, interference can be cancelled because the interference is present on the common-mode signal. Also because the differential signal is measured locally, matching problems between two sensors are limited. Therefore the amplifiers can be biased in the optimal operating region and bias offsets at the input nodes are cancelled.

In the use of local differential amplification, one selects a reference node. It is sufficient to select a common reference electrode for all differential amplifiers in the selected macrocell. If the macrocell size is within limits, the advantage of local differential amplification remains and random selection of the reference node for measuring local potentials is still possible by using post-processing of the read-out signals. One method is to define the locations of the macrocells at design time. For example (as shown in FIG. 6), the output of the first microcell 10 is used as a reference and connected to all negative inputs of the differential amplifiers within the macrocell 6.

Figure 6:
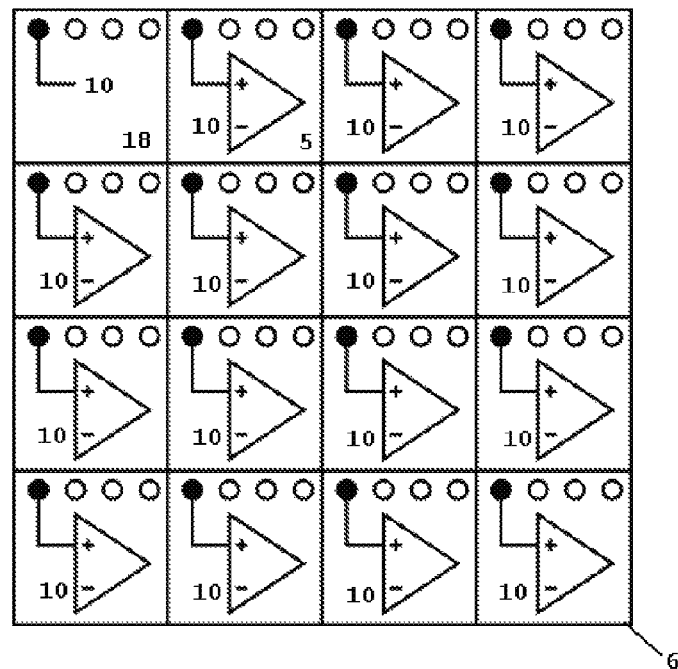
FIG. 6 is a schematic diagram illustrating the logic underlying the use of macrocells.

FIG. 6 illustrates an active macrocell 6. The squares represent microcells 5, each containing a local differential amplifier 17 with the positive input connected to one sensor selected within the amplifier, and the negative input connected to a common reference 10 coming from a microcell 18.

All outputs of the amplifiers are read out simultaneously, producing following signals:

$$\begin{cases} y_1 = x_1 - x_0 \\ y_2 = x_2 - x_0 \\ \ldots \\ y_{M-1} = x_{M-1} - x_0 \end{cases}$$

$x_i$ are the sensor nodes, $y_i$ are the outputs of the amplifiers, M is the total number of microcells within the selected macrocell. It is not always the case that node $x_0$ is the preferred reference for interpreting the output signal, for example, because this microcell itself captures signals from nearby biological cells. Suppose $x_r$ is a microcell that is defined as a useful reference node, for example, because there are no cells in that area. The output signals can be calculated with respect to microcell $x_r$ in following way:

$$\begin{cases} y_1 - y_r = x_1 - x_r \\ y_2 - y_r = x_2 - x_r \\ \ldots \\ -y_r = x_0 - x_r \\ \ldots \\ y_{M-1} - y_r = x_{M-1} - x_r \end{cases}$$

D. Chip Topology

Figure 7:
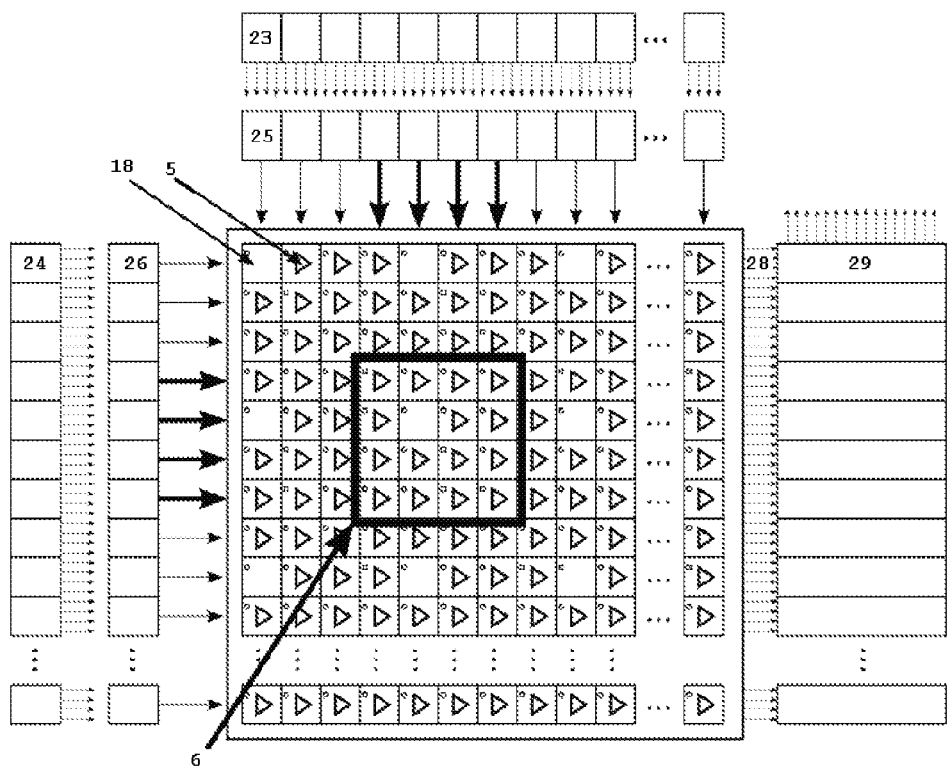
FIG. 7 schematically illustrates the topology of an interface device.

FIG. 7 schematically represents one exemplary embodiment of the sensor matrix. The different elements of the matrix are explained below.

Each microcell 5 contains a small matrix of sensors. In each such microcell, only one sensor is active. The readout of this active sensor is stored in a local memory. The microcells without a triangle, such as 18, indicate reference microcells. These reference microcells 18 do not send their signals outside the matrix. Their signals are used as a reference and are connected to the negative inputs of all differential amplifiers within the selected macrocell 6.

Microcells indicated with a triangle, such as microcell 5, contain a differential amplifier. The signal measured is the difference between the output of the active reference microcell and the output of the selected sensor. These signals 28 are transported to output multiplexers 29.

Item 23 represents a sensor matrix column address encoder. For each sensor column, there is an associated sensor column line. In this figure there are four column lines for each microcell, but this is merely an example. The column lines can contain several logical states: a logical 0, a logical 1 and a stimulation signal. The normal state is a logical 0, one or more column(s) can be selected by changing the state to a logical 1 or a stimulation signal. The sensor row and address control lines can be used to program the local sensor memory and to force a stimulation signal on a sensor node.

A sensor matrix row address encoder 24 is provided. The purpose of this encoder is analogous to that of the column address encoder. For each sensor row, there is an associated sensor row line. The row lines can take two logical states: a logical 0 and a logical 1. The normal state is a logical 1 and one or more row(s) can be selected by setting one or more lines to logical 0.

There are also microcell column encoders 25 and microcell row encoders 26. There are as many of those lines as there are microcell columns or rows. The combination of a range of active microcell column and row lines (heavy black arrows) defines the active macrocell 6. This active macrocell 6 is selected by the logical AND operation of the range of active microcell row/column lines.

Only the active microcells put their analogue output signals on the output buses 28. The number of analogue output buses depends on the macrocell size. This information goes through analogue output multiplexers 29. A set of analogue output buses is selected to send to the output of the chip for decoding.

E. Microcell Topology

Figure 8:
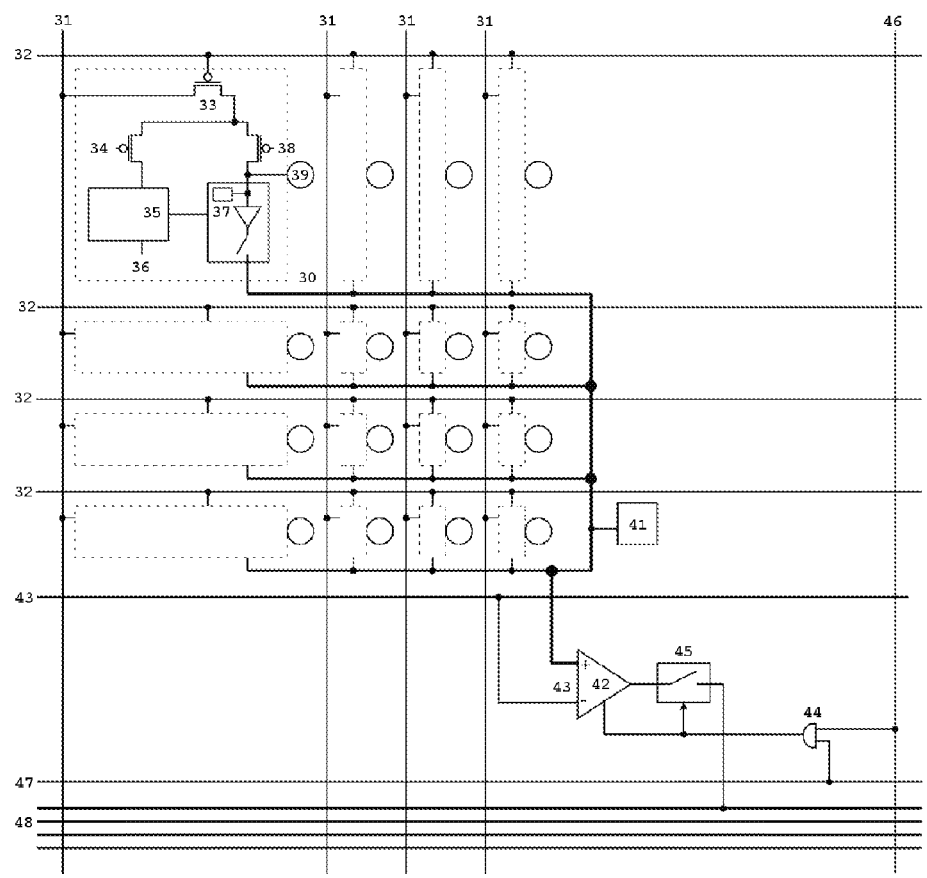
FIG. 8 is a schematic diagram illustrating the logic underlying the use of microcells.

FIG. 8 gives a schematic diagram illustrating the principle of the "microcell". Reference number 31 indicates the sensor matrix column address lines, and reference number 32 indicates the sensor matrix row address lines. For each sensor column or row, there is an associated sensor column or row line. In this figure, there are for example four column and four row lines for each microcell, but these numbers can vary in other examples. The column lines can contain several logical states: a logical 0, a logical 1 and a stimulation signal. The normal state is a logical 0; one or more column(s) can be selected by changing the state to a logical 1 or a stimulation signal. The row lines can take two logical states: a logical 0 and a logical 1. The normal state is a logical 1 and one or more row(s) can be selected by setting one or more lines to logical 0.

A transistor 33 passes a logical 1 state or a stimulation signal presented on the column line only if the row line is set at a logical 0.

A pass transistor 34 with the gate connected to a chip-global signal is named "LATCH". The normal state of this signal is logical 1. If this signal is set to logical 0, the logic signal produced by 33 can be used to set the state of the memory 35. This memory 35 is a one-bit memory (e.g. latch) which stores the state of the sensor. The normal state is a logical 0. A logical 1 represents an active sensor, which indicates that the sensor is selected for read-out. If the microcell is selected for read-out, this sensor signal is presented at the output. For each sensor, there is a memory cell. A pattern representing the locations of interest is programmed in the chip's memory. Because the locations of interest are quasi-static, this pattern may be programmed in the beginning by the use of a search algorithm, and modified minimally by the use of a tracking algorithm.

A chip-global signal named "RESET" 36 resets all memory cells to the initial state logical 0. Reference number 37 indicates an analogue circuit driven by the logical state of the memory cell. It contains an analogue switch which selects to put the read-out sensor signal 39 on the microcell-common bus 30. The microcell-common bus 30 and all switches 39 of the sensors within the microcell form an analogue multiplexer. Inside block 37, prior to the switch, an analogue amplifier with an amplification factor of 1 (a buffer) can optionally be provided in order to drive the microcell-common bus 30. In this case, it is desirable to add a biasing circuit prior to this buffer, in order to provide a proper bias voltage on floating node 39.

The gate of a pass transistor 38 is connected to a chip-global signal named "STIMULATE". The normal state of this signal is logical 1. If this signal is set to logical 0, the transistor will pass the signal produced by 33 if its signal is high enough. This can be used to force a stimulation signal on sensor node 39.

For the sensor node 39 many sensor types are possible, but in this design a capacitive sensor is used. Possible examples are: a dielectric capacitor connected to an ionic solution, or a noble metal connected to an ionic solution. This node 39 is therefore assumed to be a floating node, so a proper bias is provided either in 37 or 41. With proper biasing, connecting a noble metal in an ionic solution, the sensor behaves as a capacitive sensor.

The microcell-common bus 30 is an analogue line which selects a signal coming from one of the sensor cells, and connects it to 42.

A bias circuit 41 is implemented to provide a proper bias to the amplifier 42. Also, if 37 does not contain a bias and buffer circuit, this bias circuit provides a bias voltage for node 39 to prevent it from floating. The output of the amplifier 42 is buffered to provide enough drive current to put the analogue signal on the chip-wide analogue row output bus 46.

The negative inputs 42 of all differential amplifiers within the macrocell are connected to the macrocell-common reference signal 43. This reference can be selected from the output of a fixed microcell within the macrocell or from an external reference.

A logical AND operator 44 is used to select this microcell by combining signals 46 and 47. The output of this gate produces a microcell-wide signal named "ENABLE". This is used to put the output of the amplifier 42 on the chip-wide analogue row output bus 48 by enabling switch 45. Also this signal can be used to disable amplifier 42 to reduce power consumption.

Analogue switch 45 is used to place the output of amplifier 42 on the chip-wide analogue row output bus 46 if the microcell is enabled. There are as many of microcell column select lines 46 as there are microcell columns. Analogously, there are as many of microcell row select lines 37 as there are microcell rows.

All outputs of the switches 45 in a row on the chip are connected to the chip-wide analogue row output bus 48, enabling the analogue signal to be multiplexed and transported out of the matrix.

A matrix of actuators could be used for amperometric measurements, impedance spectroscopic measurements, actuation of MEMS-devices, or patterned stimulation of tissues. An example application is: a DNA micro array, which uses in an initial phase electrostatic attraction of antibodies by driving a specific pattern of actuators, and later on impedantiometric read-out by combining local current driving actuators with sensors. Another example application is a brain or nerve implant, where neurons have to be stimulated according to a specific pattern e.g. retina stimulation, muscle stimulation, or brain stimulation for therapeutic purposes, among other examples.

Another example application is the electronic optimization of electrode positioning with respect to neurons in neural probes. In single probe, recording the positioning of the electrodes with respect to the neurons is done mechanically by slowly advancing or withdrawing the probe while observing the electric signal. For probe arrays, this has only been done through complex assemblies that are mechanically attached to the skull (therefore limiting the application to small animals). However, the fine tuning of probe positioning is not believed to have been available in floating probe arrays. Single electrodes are replaced with clusters of electrodes. Using the interfaces described herein, a probe comprising a large number of electrodes can be used, out of which the best (e.g., the closest to neurons) are selected electronically. As no mechanical movement is involved, each cluster of electrodes can be adjusted independently from the others. The lack of mechanical movement also enables the probe to remain more stably attached to the brain tissue. As an example, suppose that a probe would originally contain five electrodes along its shaft. Using an interface as described herein, each of those electrodes can be replaced by a group of 10 electrodes. In other words, the interface device can also be used as a 1-dimensional application.

The invention claimed is:

1. An interface device for providing access to a network to be monitored, the interface device comprising:
    a chip memory; and
    a plurality of microcells arranged in rows and columns, each microcell in the plurality of microcells comprising a matrix of elements, a local multiplexing circuit, and an amplifier, the elements being sensors and/or actuators, each element having a memory cell of the chip memory storing a state of the element, wherein the local multiplexing circuit is configured for selecting an active element based on the states of the elements stored in the memory cells and leave other elements unconnected, wherein the amplifier is configured to generate an output of the microcell based on an output of the active element, wherein an active plurality of microcells of the plurality of microcells is selected according to a programmed pattern stored in the chip memory, and wherein the interface device is configured to readout the respective generated outputs of the active plurality of microcells simultaneously.

2. The interface device according to claim 1 wherein the plurality of microcells are configured to be arranged as one or more macrocells.

3. The interface device according to claim 1, wherein the amplifier comprises a differential amplifier.

4. A method for accessing a signal in an interface device according to claim 1, the method comprising the steps of:
    determining a selection of an active plurality of microcells from a plurality of microcells of the interface device according to a programmed pattern, the plurality of microcells arranged in rows and columns, each microcell in the plurality of microcells comprising a matrix of elements, a local multiplexing circuit, and an amplifier, the elements being sensors and/or an actuators, each element having a memory cell of a chip memory of the interface device for storing a state of the element, wherein the local multiplexing circuit is configured for selecting an active element based on the states of the elements stored in the memory cells and leave other elements unconnected, wherein the amplifier is configured to generate an output of the microcell based on an output of the active element, and wherein the programmed pattern is stored in the chip memory; and
    reading out the respective generated outputs of the active plurality of microcells simultaneously.

5. The method according to claim 4, wherein the interface accesses a network of electrically-active biological cells.

6. The method according to claim 4, wherein the step of determining the selection is related to the position of neurons.

7. The interface device according to claim 3, wherein each microcell in the plurality of microcells further comprises a biasing circuit for providing a bias to the differential amplifier.

8. The interface device according to claim 3, wherein the differential amplifier is configured to generate an output of the microcell based on a difference between an output of the active element and a reference element.

9. The interface device according to claim 8, wherein the reference element comprises a sensor and/or an actuator.

10. The interface device according to claim 1, wherein the local multiplexing circuit comprises, for each element in each microcell, analogue circuitry driven by the state of the memory cell of that element for selecting a read-out signal for the element.

11. The method according to claim 4, wherein the amplifier comprises a differential amplifier.

12. The method according to claim 11, wherein the differential amplifier is configured to generate an output of the microcell based on a difference between an output of the active element and a reference element.

13. The method according to claim 12, wherein the reference element comprises a sensor and/or an actuator.

14. The method according to claim 4, wherein the local multiplexing circuit comprises, for each element in each microcell, analogue circuitry driven by the state of the memory cell of that element for selecting a read-out signal for the element.

* * * * *